United States Patent
Matlock

(10) Patent No.: US 7,555,327 B2
(45) Date of Patent: Jun. 30, 2009

(54) FOLDING MEDICAL SENSOR AND TECHNIQUE FOR USING THE SAME

(75) Inventor: George L. Matlock, Pleasanton, CA (US)

(73) Assignee: Nellcor Puritan Bennett LLC, Boulder, CO (US)

(*) Notice: Subject to any disclaimer, the term of this patent is extended or adjusted under 35 U.S.C. 154(b) by 458 days.

(21) Appl. No.: 11/241,014

(22) Filed: Sep. 30, 2005

(65) Prior Publication Data

US 2007/0078317 A1    Apr. 5, 2007

(51) Int. Cl.
*A61B 5/1455* (2006.01)
(52) U.S. Cl. ...................................... 600/344
(58) Field of Classification Search .............. 600/344, 600/310, 322, 323
See application file for complete search history.

(56) References Cited

U.S. PATENT DOCUMENTS

| | | | |
|---|---|---|---|
| 2,699,585 A * | 1/1955 | Patterson ............ 24/16 R |
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsey et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger |
| 4,694,833 A | 9/1987 | Hamaguri |

(Continued)

FOREIGN PATENT DOCUMENTS

DE    3405444    8/1985

(Continued)

OTHER PUBLICATIONS

Envitec, SoftTip SpO2 Finger Sensors Full Encapsulated Silicone Sensors Range, www.envitec-dk.com, Glostrup, Denmark.

(Continued)

*Primary Examiner*—Eric F Winakur
*Assistant Examiner*—Etsub D Berhanu

(57) ABSTRACT

A sensor assembly is provided that includes a frame upon which electrical and optical components may be disposed and a covering, such as an overmold coating, provided about the frame. The frame may be moved between an open and a closed configuration, such as during the manufacture of the sensor assembly. The sensor assembly includes a retaining component configured to hold the sensor in the closed configuration when engaged. In one embodiment, the sensor may be placed on a patient's finger, toe, ear, and so forth to obtain pulse oximetry or other physiological measurements.

20 Claims, 4 Drawing Sheets

U.S. PATENT DOCUMENTS

| | | |
|---|---|---|
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE033,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp, Jr. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |

| | | | | | |
|---|---|---|---|---|---|
| 5,349,519 A | 9/1994 | Kaestle | 5,577,500 A | 11/1996 | Potratz |
| 5,349,952 A | 9/1994 | McCarthy et al. | 5,582,169 A | 12/1996 | Oda et al. |
| 5,349,953 A | 9/1994 | McCarthy et al. | 5,584,296 A | 12/1996 | Cui et al. |
| 5,351,685 A | 10/1994 | Potratz | 5,588,425 A | 12/1996 | Sackner et al. |
| 5,353,799 A | 10/1994 | Chance | 5,588,427 A | 12/1996 | Tien |
| 5,355,880 A | 10/1994 | Thomas et al. | 5,590,652 A | 1/1997 | Inai |
| 5,355,882 A | 10/1994 | Ukawa et al. | 5,595,176 A | 1/1997 | Yamaura |
| 5,361,758 A | 11/1994 | Hall et al. | 5,596,986 A | 1/1997 | Goldfarb |
| 5,365,066 A | 11/1994 | Krueger, Jr. et al. | 5,611,337 A | 3/1997 | Bukta |
| 5,368,025 A | 11/1994 | Young et al. | 5,617,852 A | 4/1997 | MacGregor |
| 5,368,026 A | 11/1994 | Swedlow et al. | 5,619,992 A | 4/1997 | Guthrie et al. |
| 5,368,224 A | 11/1994 | Richardson et al. | 5,626,140 A | 5/1997 | Feldman et al. |
| 5,372,136 A | 12/1994 | Steuer et al. | 5,630,413 A | 5/1997 | Thomas et al. |
| 5,377,675 A | 1/1995 | Ruskewicz et al. | 5,632,272 A | 5/1997 | Diab et al. |
| 5,385,143 A | 1/1995 | Aoyagi | 5,632,273 A | 5/1997 | Suzuki |
| 5,387,122 A | 2/1995 | Goldberger et al. | 5,634,459 A | 6/1997 | Gardosi |
| 5,390,670 A | 2/1995 | Centa et al. | 5,638,593 A | 6/1997 | Gerhardt et al. |
| 5,392,777 A | 2/1995 | Swedlow et al. | 5,638,816 A | 6/1997 | Kiani-Azarbayjany et al. |
| 5,398,680 A | 3/1995 | Polson et al. | 5,638,818 A | 6/1997 | Diab et al. |
| 5,402,777 A | 4/1995 | Warring et al. | 5,645,060 A | 7/1997 | Yorkey et al. |
| 5,402,779 A | 4/1995 | Chen et al. | 5,645,440 A | 7/1997 | Tobler et al. |
| 5,411,023 A | 5/1995 | Morris, Sr. et al. | 5,660,567 A | 8/1997 | Nierlich et al. |
| 5,411,024 A | 5/1995 | Thomas et al. | 5,662,105 A | 9/1997 | Tien |
| 5,413,099 A | 5/1995 | Schmidt et al. | 5,662,106 A | 9/1997 | Swedlow et al. |
| 5,413,100 A | 5/1995 | Barthelemy et al. | 5,664,270 A | 9/1997 | Bell et al. |
| 5,413,101 A | 5/1995 | Sugiura | 5,666,952 A | 9/1997 | Fuse et al. |
| 5,413,102 A | 5/1995 | Schmidt et al. | 5,671,529 A | 9/1997 | Nelson |
| 5,417,207 A | 5/1995 | Young et al. | 5,673,692 A | 10/1997 | Schulze et al. |
| 5,421,329 A | 6/1995 | Casciani et al. | 5,673,693 A | 10/1997 | Solenberger |
| 5,425,360 A | 6/1995 | Nelson | 5,676,139 A | 10/1997 | Goldberger et al. |
| 5,425,362 A | 6/1995 | Siker et al. | 5,676,141 A | 10/1997 | Hollub |
| 5,427,093 A | 6/1995 | Ogawa et al. | 5,678,544 A | 10/1997 | DeLonzor et al. |
| 5,429,128 A | 7/1995 | Cadell et al. | 5,680,857 A | 10/1997 | Pelikan et al. |
| 5,429,129 A | 7/1995 | Lovejoy et al. | 5,685,299 A | 11/1997 | Diab et al. |
| 5,431,159 A | 7/1995 | Baker et al. | 5,685,301 A | 11/1997 | Klomhaus |
| 5,431,170 A | 7/1995 | Mathews | 5,687,719 A | 11/1997 | Sato et al. |
| 5,437,275 A | 8/1995 | Amundsen et al. | 5,687,722 A | 11/1997 | Tien et al. |
| 5,438,986 A | 8/1995 | Disch et al. | 5,692,503 A | 12/1997 | Kuenstner |
| 5,448,991 A | 9/1995 | Polson et al. | 5,692,505 A | 12/1997 | Fouts |
| 5,452,717 A | 9/1995 | Branigan et al. | 5,709,205 A | 1/1998 | Bukta |
| 5,465,714 A | 11/1995 | Scheuing | 5,713,355 A | 2/1998 | Richardson et al. |
| 5,469,845 A | 11/1995 | DeLonzor et al. | 5,724,967 A | 3/1998 | Venkatachalam |
| 5,482,034 A | 1/1996 | Lewis et al. | 5,727,547 A | 3/1998 | Levinson et al. |
| 5,482,036 A | 1/1996 | Diab et al. | 5,730,124 A | 3/1998 | Yamauchi |
| 5,485,847 A | 1/1996 | Baker, Jr. | 5,731,582 A | 3/1998 | West |
| 5,490,505 A | 2/1996 | Diab et al. | D393,830 S | 4/1998 | Tobler et al. |
| 5,490,523 A | 2/1996 | Isaacson et al. | 5,743,260 A | 4/1998 | Chung et al. |
| 5,491,299 A | 2/1996 | Naylor et al. | 5,743,262 A | 4/1998 | Lepper, Jr. et al. |
| 5,494,032 A | 2/1996 | Robinson et al. | 5,743,263 A | 4/1998 | Baker, Jr. |
| 5,494,043 A | 2/1996 | O'Sullivan et al. | 5,746,206 A | 5/1998 | Mannheimer |
| 5,497,771 A | 3/1996 | Rosenheimer | 5,746,697 A | 5/1998 | Swedlow et al. |
| 5,499,627 A | 3/1996 | Steuer et al. | 5,752,914 A | 5/1998 | DeLonzor et al. |
| 5,503,148 A | 4/1996 | Pologe et al. | 5,755,226 A | 5/1998 | Carim et al. |
| 5,505,199 A | 4/1996 | Kim | 5,758,644 A | 6/1998 | Diab et al. |
| 5,507,286 A | 4/1996 | Solenberger | 5,760,910 A | 6/1998 | Lepper, Jr. et al. |
| 5,511,546 A | 4/1996 | Hon | 5,766,125 A | 6/1998 | Aoyagi et al. |
| 5,517,988 A | 5/1996 | Gerhard | 5,766,127 A | 6/1998 | Pologe et al. |
| 5,520,177 A | 5/1996 | Ogawa et al. | 5,769,785 A | 6/1998 | Diab et al. |
| 5,521,851 A | 5/1996 | Wei et al. | 5,772,587 A | 6/1998 | Gratton et al. |
| 5,522,388 A | 6/1996 | Ishikawa et al. | 5,774,213 A | 6/1998 | Trebino et al. |
| 5,524,617 A | 6/1996 | Mannheimer | 5,776,058 A | 7/1998 | Levinson et al. |
| 5,529,064 A | 6/1996 | Rall et al. | 5,776,059 A | 7/1998 | Kaestle et al. |
| 5,533,507 A | 7/1996 | Potratz | 5,779,630 A | 7/1998 | Fein et al. |
| 5,551,423 A | 9/1996 | Sugiura | 5,779,631 A | 7/1998 | Chance |
| 5,551,424 A | 9/1996 | Morrison et al. | 5,782,237 A | 7/1998 | Casciani et al. |
| 5,553,614 A | 9/1996 | Chance | 5,782,756 A | 7/1998 | Mannheimer |
| 5,553,615 A | 9/1996 | Carim et al. | 5,782,757 A | 7/1998 | Diab et al. |
| 5,555,882 A | 9/1996 | Richardson et al. | 5,782,758 A | 7/1998 | Ausec et al. |
| 5,558,096 A | 9/1996 | Palatnik | 5,786,592 A | 7/1998 | Hök |
| 5,560,355 A | 10/1996 | Merchant et al. | 5,788,634 A | 8/1998 | Suda et al. |
| 5,564,417 A | 10/1996 | Chance | 5,790,729 A | 8/1998 | Pologe et al. |
| 5,575,284 A | 11/1996 | Athan et al. | 5,792,052 A | 8/1998 | Isaacson et al. |
| 5,575,285 A | 11/1996 | Takanashi et al. | 5,795,292 A | 8/1998 | Lewis et al. |

| | | | | | | |
|---|---|---|---|---|---|---|
| 5,797,841 A | 8/1998 | DeLonzor et al. | | 5,997,343 A | 12/1999 | Mills et al. |
| 5,800,348 A | 9/1998 | Kaestle | | 5,999,834 A | 12/1999 | Wang et al. |
| 5,800,349 A | 9/1998 | Isaacson et al. | | 6,002,952 A | 12/1999 | Diab et al. |
| 5,803,910 A | 9/1998 | Potratz | | 6,005,658 A | 12/1999 | Kaluza et al. |
| 5,807,246 A | 9/1998 | Sakaguchi et al. | | 6,006,120 A | 12/1999 | Levin |
| 5,807,247 A | 9/1998 | Merchant et al. | | 6,011,985 A | 1/2000 | Athan et al. |
| 5,807,248 A | 9/1998 | Mills | | 6,011,986 A | 1/2000 | Diab et al. |
| 5,810,723 A | 9/1998 | Aldrich | | 6,014,576 A | 1/2000 | Raley et al. |
| 5,810,724 A | 9/1998 | Gronvall | | 6,018,673 A | 1/2000 | Chin et al. |
| 5,813,980 A | 9/1998 | Levinson et al. | | 6,018,674 A | 1/2000 | Aronow |
| 5,817,008 A | 10/1998 | Rafert et al. | | 6,022,321 A | 2/2000 | Amano et al. |
| 5,817,009 A | 10/1998 | Rosenheimer et al. | | 6,023,541 A | 2/2000 | Merchant et al. |
| 5,817,010 A | 10/1998 | Hibl | | 6,026,312 A | 2/2000 | Shemwell et al. |
| 5,818,985 A | 10/1998 | Merchant et al. | | 6,026,314 A | 2/2000 | Amerov et al. |
| 5,820,550 A | 10/1998 | Polson et al. | | 6,031,603 A | 2/2000 | Fine et al. |
| 5,823,950 A | 10/1998 | Diab et al. | | 6,035,223 A | 3/2000 | Baker, Jr. |
| 5,823,952 A | 10/1998 | Levinson et al. | | 6,036,642 A | 3/2000 | Diab et al. |
| 5,827,179 A | 10/1998 | Lichter et al. | | 6,041,247 A | 3/2000 | Weckstrom et al. |
| 5,827,182 A | 10/1998 | Raley et al. | | 6,044,283 A | 3/2000 | Fein et al. |
| 5,829,439 A | 11/1998 | Yokosawa et al. | | 6,047,201 A | 4/2000 | Jackson, III |
| 5,830,135 A | 11/1998 | Bosque et al. | | 6,055,447 A | 4/2000 | Weil et al. |
| 5,830,136 A | 11/1998 | DeLonzor et al. | | 6,061,584 A | 5/2000 | Lovejoy et al. |
| 5,830,137 A | 11/1998 | Scharf | | 6,064,898 A | 5/2000 | Aldrich |
| 5,839,439 A | 11/1998 | Nierlich et al. | | 6,064,899 A | 5/2000 | Fein et al. |
| 5,842,979 A | 12/1998 | Jarman | | 6,067,462 A | 5/2000 | Diab et al. |
| 5,842,981 A | 12/1998 | Larsen et al. | | 6,073,038 A | 6/2000 | Wang et al. |
| 5,842,982 A | 12/1998 | Mannheimer | | 6,078,829 A | 6/2000 | Uchida |
| 5,846,190 A | 12/1998 | Woehrle | | 6,078,833 A | 6/2000 | Hueber |
| 5,851,178 A | 12/1998 | Aronow | | 6,081,735 A | 6/2000 | Diab et al. |
| 5,851,179 A | 12/1998 | Ritson et al. | | 6,083,157 A | 7/2000 | Noller |
| 5,853,364 A | 12/1998 | Baker, Jr. et al. | | 6,083,172 A | 7/2000 | Baker, Jr. et al. |
| 5,860,919 A | 1/1999 | Kiani-Azarbayjany et al. | | 6,088,607 A | 7/2000 | Diab et al. |
| 5,865,736 A | 2/1999 | Baker, Jr. et al. | | 6,094,592 A | 7/2000 | Yorkey et al. |
| 5,879,294 A | 3/1999 | Anderson et al. | | 6,095,974 A | 8/2000 | Shemwell et al. |
| 5,885,213 A | 3/1999 | Richardson et al. | | 6,104,938 A | 8/2000 | Huiku et al. |
| 5,890,929 A | 4/1999 | Mills et al. | | 6,104,939 A | 8/2000 | Groner |
| 5,891,021 A | 4/1999 | Dillon et al. | | 6,112,107 A | 8/2000 | Hannula |
| 5,891,022 A | 4/1999 | Pologe | | 6,113,541 A | 9/2000 | Dias et al. |
| 5,891,024 A | 4/1999 | Jarman et al. | | 6,115,621 A | 9/2000 | Chin |
| 5,891,025 A | 4/1999 | Buschmann et al. | | 6,122,535 A | 9/2000 | Kaestle et al. |
| 5,891,026 A | 4/1999 | Wang et al. | | 6,133,994 A | 10/2000 | Mathews et al. |
| 5,902,235 A | 5/1999 | Lewis et al. | | 6,135,952 A | 10/2000 | Coetzee |
| 5,910,108 A | 6/1999 | Solenberger | | 6,144,444 A | 11/2000 | Haworth et al. |
| 5,911,690 A | 6/1999 | Rall | | 6,144,867 A | 11/2000 | Walker et al. |
| 5,912,656 A | 6/1999 | Tham et al. | | 6,144,868 A | 11/2000 | Parker |
| 5,913,819 A | 6/1999 | Taylor et al. | | 6,149,481 A | 11/2000 | Wang et al. |
| 5,916,154 A | 6/1999 | Hobbs et al. | | 6,151,107 A | 11/2000 | Schöllermann et al. |
| 5,916,155 A | 6/1999 | Levinson et al. | | 6,151,516 A | 11/2000 | Kiani-Azarbayjani et al. |
| 5,919,133 A | 7/1999 | Taylor et al. | | 6,151,518 A | 11/2000 | Hayashi |
| 5,919,134 A | 7/1999 | Diab | | 6,152,754 A | 11/2000 | Gerhardt et al. |
| 5,920,263 A | 7/1999 | Huttenhoff et al. | | 6,154,667 A | 11/2000 | Miura et al. |
| 5,921,921 A | 7/1999 | Potratz et al. | | 6,157,850 A | 12/2000 | Diab et al. |
| 5,922,607 A | 7/1999 | Bernreuter | | 6,159,147 A | 12/2000 | Lichter |
| 5,924,979 A | 7/1999 | Swedlow et al. | | 6,163,175 A | 12/2000 | Sharpe-Geisler |
| 5,924,980 A | 7/1999 | Coetzee | | 6,163,715 A | 12/2000 | Larsen et al. |
| 5,924,982 A | 7/1999 | Chin | | 6,165,005 A | 12/2000 | Mills et al. |
| 5,924,985 A | 7/1999 | Jones | | 6,173,196 B1 | 1/2001 | Delonzor et al. |
| 5,934,277 A | 8/1999 | Mortz | | 6,178,343 B1 | 1/2001 | Bindszus et al. |
| 5,934,925 A | 8/1999 | Tobler et al. | | 6,179,159 B1 | 1/2001 | Gurley |
| 5,940,182 A | 8/1999 | Lepper, Jr. et al. | | 6,181,958 B1 | 1/2001 | Steuer et al. |
| 5,954,644 A | 9/1999 | Dettling et al. | | 6,181,959 B1 | 1/2001 | Schöllermann et al. |
| 5,957,840 A | 9/1999 | Terasawa et al. | | 6,184,521 B1 | 2/2001 | Coffin, IV et al. |
| 5,960,610 A | 10/1999 | Levinson et al. | | 6,188,470 B1 | 2/2001 | Grace |
| 5,961,450 A | 10/1999 | Merchant et al. | | 6,192,260 B1 | 2/2001 | Chance |
| 5,961,452 A | 10/1999 | Chung et al. | | 6,195,575 B1 | 2/2001 | Levinson |
| 5,964,701 A | 10/1999 | Asada et al. | | 6,198,951 B1 | 3/2001 | Kosuda et al. |
| 5,971,930 A | 10/1999 | Elghazzawi | | 6,206,830 B1 | 3/2001 | Diab et al. |
| 5,978,691 A | 11/1999 | Mills | | 6,213,952 B1 | 4/2001 | Finarov et al. |
| 5,978,693 A | 11/1999 | Hamilton et al. | | 6,217,523 B1 | 4/2001 | Amano et al. |
| 5,983,120 A | 11/1999 | Groner et al. | | 6,222,189 B1 | 4/2001 | Misner et al. |
| 5,983,122 A | 11/1999 | Jarman et al. | | 6,223,064 B1 | 4/2001 | Lynn |
| 5,987,343 A | 11/1999 | Kinast | | 6,226,539 B1 | 5/2001 | Potratz |
| 5,995,859 A | 11/1999 | Takahashi | | 6,226,540 B1 | 5/2001 | Bernreuter et al. |

| | | |
|---|---|---|
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |

| | | |
|---|---|---|
| 6,650,917 B2 | 11/2003 | Diab et al. |
| 6,650,918 B2 | 11/2003 | Terry |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE038,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE038,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow et al. |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boaz et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |

| | | | | | |
|---|---|---|---|---|---|
| 7,096,052 B2 | 8/2006 | Mason et al. | 2004/0064020 A1 | 4/2004 | Diab et al. |
| 7,096,054 B2 | 8/2006 | Abdul-Hafiz et al. | 2004/0068164 A1 | 4/2004 | Diab et al. |
| 7,107,088 B2 | 9/2006 | Aceti | 2004/0087846 A1 | 5/2004 | Wasserman |
| 7,113,815 B2 | 9/2006 | O'Neil et al. | 2004/0092805 A1 | 5/2004 | Yarita |
| 7,123,950 B2 | 10/2006 | Mannheimer | 2004/0097797 A1 | 5/2004 | Porges et al. |
| 7,127,278 B2 | 10/2006 | Melker et al. | 2004/0098009 A1 | 5/2004 | Boecker et al. |
| 7,130,671 B2 | 10/2006 | Baker, Jr. et al. | 2004/0107065 A1 | 6/2004 | Al-Ali et al. |
| 7,132,641 B2 | 11/2006 | Schulz et al. | 2004/0116788 A1 | 6/2004 | Chernoguz et al. |
| 7,133,711 B2 | 11/2006 | Chernoguz et al. | 2004/0116789 A1 | 6/2004 | Boaz et al. |
| 7,139,599 B2 | 11/2006 | Terry | 2004/0117891 A1 | 6/2004 | Hannula et al. |
| 7,142,901 B2 | 11/2006 | Kiani et al. | 2004/0122300 A1 | 6/2004 | Boas et al. |
| 7,190,986 B1 * | 3/2007 | Hannula et al. ............ 600/323 | 2004/0122302 A1 | 6/2004 | Mason et al. |
| 7,190,987 B2 | 3/2007 | Lindekugel et al. | 2004/0133087 A1 | 7/2004 | Ali et al. |
| 7,198,778 B2 | 4/2007 | Achilefu et al. | 2004/0133088 A1 | 7/2004 | Al-Ali et al. |
| 7,215,984 B2 | 5/2007 | Diab et al. | 2004/0138538 A1 | 7/2004 | Stetson |
| 7,225,006 B2 | 5/2007 | Al-Ali et al. | 2004/0138540 A1 | 7/2004 | Baker, Jr. et al. |
| 7,228,161 B2 | 6/2007 | Chin | 2004/0143172 A1 | 7/2004 | Fudge et al. |
| 7,236,881 B2 | 6/2007 | Liu et al. | 2004/0147821 A1 | 7/2004 | Al-Ali et al. |
| 7,248,910 B2 | 7/2007 | Li et al. | 2004/0147822 A1 | 7/2004 | Al-Ali et al. |
| 7,254,433 B2 | 8/2007 | Diab et al. | 2004/0147823 A1 | 7/2004 | Kiani et al. |
| 7,254,434 B2 | 8/2007 | Schulz et al. | 2004/0147824 A1 | 7/2004 | Diab et al. |
| 7,280,858 B2 | 10/2007 | Al-Ali et al. | 2004/0152965 A1 | 8/2004 | Diab et al. |
| 7,295,866 B2 | 11/2007 | Al-Ali et al. | 2004/0158134 A1 | 8/2004 | Diab et al. |
| 7,305,262 B2 | 12/2007 | Brodnick et al. | 2004/0158135 A1 | 8/2004 | Baker, Jr. et al. |
| 7,315,753 B2 | 1/2008 | Baker, Jr. et al. | 2004/0162472 A1 | 8/2004 | Berson et al. |
| 2001/0021803 A1 | 9/2001 | Blank et al. | 2004/0167381 A1 | 8/2004 | Lichter |
| 2001/0051767 A1 | 12/2001 | Williams et al. | 2004/0171920 A1 | 9/2004 | Mannheimer et al. |
| 2002/0016537 A1 | 2/2002 | Muz et al. | 2004/0171948 A1 | 9/2004 | Terry |
| 2002/0026109 A1 | 2/2002 | Diab et al. | 2004/0176671 A1 | 9/2004 | Fine et al. |
| 2002/0028990 A1 | 3/2002 | Shepherd et al. | 2004/0181133 A1 | 9/2004 | Al-Ali et al. |
| 2002/0038078 A1 | 3/2002 | Ito | 2004/0181134 A1 | 9/2004 | Baker, Jr. et al. |
| 2002/0042558 A1 | 4/2002 | Mendelson | 2004/0186358 A1 | 9/2004 | Chernow et al. |
| 2002/0068859 A1 | 6/2002 | Knopp | 2004/0199063 A1 | 10/2004 | O'Neil et al. |
| 2002/0072681 A1 | 6/2002 | Schnall | 2004/0204636 A1 | 10/2004 | Diab et al. |
| 2002/0116797 A1 | 8/2002 | Modgil et al. | 2004/0204637 A1 | 10/2004 | Diab et al. |
| 2002/0128544 A1 | 9/2002 | Diab et al. | 2004/0204865 A1 | 10/2004 | Lee et al. |
| 2002/0133067 A1 | 9/2002 | Jackson, III | 2004/0210146 A1 | 10/2004 | Diab et al. |
| 2002/0156354 A1 | 10/2002 | Larson | 2004/0215069 A1 | 10/2004 | Mannheimer |
| 2002/0173706 A1 | 11/2002 | Takatani | 2004/0215085 A1 | 10/2004 | Schnall |
| 2002/0173709 A1 | 11/2002 | Fine et al. | 2004/0230107 A1 | 11/2004 | Asada et al. |
| 2002/0190863 A1 | 12/2002 | Lynn | 2004/0230108 A1 | 11/2004 | Melker et al. |
| 2002/0198442 A1 | 12/2002 | Rantala et al. | 2004/0236196 A1 | 11/2004 | Diab et al. |
| 2003/0018243 A1 | 1/2003 | Gerhardt et al. | 2004/0242980 A1 | 12/2004 | Kiani et al. |
| 2003/0036690 A1 | 2/2003 | Geddes et al. | 2004/0249252 A1 | 12/2004 | Fine et al. |
| 2003/0045785 A1 | 3/2003 | Diab et al. | 2004/0257557 A1 | 12/2004 | Block et al. |
| 2003/0073889 A1 | 4/2003 | Keilbach et al. | 2004/0260161 A1 | 12/2004 | Melker et al. |
| 2003/0073890 A1 | 4/2003 | Hanna | 2004/0267103 A1 | 12/2004 | Li et al. |
| 2003/0100840 A1 | 5/2003 | Sugiura et al. | 2004/0267104 A1 | 12/2004 | Hannula et al. |
| 2003/0132495 A1 | 7/2003 | Mills et al. | 2004/0267140 A1 | 12/2004 | Ito et al. |
| 2003/0135099 A1 | 7/2003 | Al-Ali | 2005/0004479 A1 | 1/2005 | Townsend et al. |
| 2003/0162414 A1 | 8/2003 | Schulz | 2005/0010092 A1 | 1/2005 | Weber et al. |
| 2003/0171662 A1 | 9/2003 | O'Connor et al. | 2005/0014999 A1 | 1/2005 | Rahe-Meyer |
| 2003/0176776 A1 | 9/2003 | Huiku | 2005/0020887 A1 | 1/2005 | Goldberg |
| 2003/0181799 A1 | 9/2003 | Lindekugel et al. | 2005/0020894 A1 | 1/2005 | Norris et al. |
| 2003/0187337 A1 | 10/2003 | Tarassenko et al. | 2005/0033131 A1 | 2/2005 | Chen |
| 2003/0195402 A1 | 10/2003 | Fein et al. | 2005/0043599 A1 | 2/2005 | O'Mara |
| 2003/0197679 A1 | 10/2003 | Ali et al. | 2005/0043600 A1 | 2/2005 | Diab et al. |
| 2003/0212316 A1 | 11/2003 | Leiden et al. | 2005/0049468 A1 | 3/2005 | Carlson |
| 2003/0225323 A1 | 12/2003 | Kiani et al. | 2005/0049470 A1 | 3/2005 | Terry |
| 2003/0225337 A1 | 12/2003 | Scharf et al. | 2005/0049471 A1 | 3/2005 | Aceti |
| 2003/0236452 A1 | 12/2003 | Melker et al. | 2005/0070773 A1 | 3/2005 | Chin |
| 2003/0236647 A1 | 12/2003 | Yoon et al. | 2005/0075546 A1 | 4/2005 | Samsoondar |
| 2004/0006261 A1 | 1/2004 | Swedlow et al. | 2005/0075550 A1 | 4/2005 | Lindekugel |
| 2004/0010188 A1 | 1/2004 | Wasserman et al. | 2005/0085704 A1 | 4/2005 | Schulz |
| 2004/0024297 A1 | 2/2004 | Chen et al. | 2005/0090720 A1 | 4/2005 | Wu |
| 2004/0024326 A1 | 2/2004 | Yeo et al. | 2005/0197548 A1 | 9/2005 | Dietiker |
| 2004/0034293 A1 | 2/2004 | Kimball | 2005/0228248 A1 | 10/2005 | Dietiker |
| 2004/0039272 A1 | 2/2004 | Abdul-Hafiz | 2005/0256386 A1 | 11/2005 | Chan |
| 2004/0039273 A1 | 2/2004 | Terry | 2005/0277819 A1 | 12/2005 | Kiani et al. |
| 2004/0054269 A1 | 3/2004 | Rantala et al. | 2006/0020179 A1 | 1/2006 | Anderson |
| 2004/0054291 A1 | 3/2004 | Schulz et al. | 2006/0030764 A1 | 2/2006 | Porges |
| 2004/0059209 A1 | 3/2004 | Al-Ali et al. | 2006/0058594 A1 | 3/2006 | Ishizuka et al. |
| 2004/0059210 A1 | 3/2004 | Stetson | 2006/0074280 A1 | 4/2006 | Martis |

| | | | |
|---|---|---|---|
| 2006/0084852 A1 | 4/2006 | Mason et al. | |
| 2006/0084878 A1 | 4/2006 | Banet | |
| 2006/0089547 A1 | 4/2006 | Sarussi | |
| 2006/0106294 A1 | 5/2006 | Maser et al. | |
| 2006/0122517 A1 | 6/2006 | Banet | |
| 2006/0129039 A1 | 6/2006 | Lindner | |
| 2006/0155198 A1 | 7/2006 | Schmid | |
| 2006/0173257 A1 | 8/2006 | Nagai | |
| 2007/0032708 A1 | 2/2007 | Eghbal et al. | |
| 2007/0032709 A1 | 2/2007 | Coakley et al. | |
| 2007/0032710 A1 | 2/2007 | Raridan, Jr. et al. | |
| 2007/0032712 A1 | 2/2007 | Raridan et al. | |
| 2007/0073126 A1 | 3/2007 | Raridan, Jr. | |

FOREIGN PATENT DOCUMENTS

| | | |
|---|---|---|
| DE | 3516338 | 11/1986 |
| DE | 37 03 458 | 8/1988 |
| DE | 3938759 | 5/1991 |
| DE | 4210102 A1 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 A1 | 9/1997 |
| DE | 19647877 A1 | 4/1998 |
| DE | 10030862 | 1/2002 |
| DE | 20318882 U1 | 4/2004 |
| EP | 0127947 | 5/1984 |
| EP | 00194105 B1 | 9/1986 |
| EP | 00204459 A3 | 12/1986 |
| EP | 0 262 779 | 4/1988 |
| EP | 0315040 | 10/1988 |
| EP | 0314331 | 5/1989 |
| EP | 00352923 | 1/1990 |
| EP | 0 360 977 | 4/1990 |
| EP | 00430340 A3 | 6/1991 |
| EP | 435 500 | 7/1991 |
| EP | 0572684 | 5/1992 |
| EP | 00497021 A1 | 8/1992 |
| EP | 0529412 | 8/1992 |
| EP | 0531631 | 9/1992 |
| EP | 0566354 | 4/1993 |
| EP | 0587009 | 8/1993 |
| EP | 00630203 B1 | 9/1993 |
| EP | 0 572 684 | 12/1993 |
| EP | 00615723 | 9/1994 |
| EP | 00702931 A1 | 3/1996 |
| EP | 00724860 A1 | 8/1996 |
| EP | 00793942 A3 | 9/1997 |
| EP | 0 864 293 | 9/1998 |
| EP | 01006863 B1 | 10/1998 |
| EP | 01006864 B1 | 10/1998 |
| EP | 0875199 | 11/1998 |
| EP | 00998214 A1 | 12/1998 |
| EP | 0898933 | 3/1999 |
| EP | 01332713 A1 | 8/2003 |
| EP | 01469773 A1 | 8/2003 |
| EP | 1502529 | 7/2004 |
| EP | 1491135 | 12/2004 |
| EP | 1584287 | 12/2005 |
| FR | 2685865 | 1/1992 |
| GB | 2 259 545 | 3/1993 |
| JP | 63275325 A | 11/1988 |
| JP | 2013450 A | 1/1990 |
| JP | 2111343 A | 4/1990 |
| JP | 02-191434 | 7/1990 |
| JP | 2237544 A | 9/1990 |
| JP | 03-173536 | 7/1991 |
| JP | 3170866 A | 7/1991 |
| JP | 3245042 A | 10/1991 |
| JP | 4174648 A | 6/1992 |
| JP | 4191642 A | 7/1992 |
| JP | 4332536 A | 11/1992 |
| JP | 3124073 B | 3/1993 |
| JP | 5049624 A | 3/1993 |
| JP | 5049625 A | 3/1993 |
| JP | 3115374 B | 4/1993 |
| JP | 2005/200031 | 8/1993 |
| JP | 5212016 A | 8/1993 |
| JP | 06014906 | 1/1994 |
| JP | 6016774 B2 | 3/1994 |
| JP | 3116255 B | 4/1994 |
| JP | 6029504 U | 4/1994 |
| JP | 6098881 A | 4/1994 |
| JP | 06-154177 | 6/1994 |
| JP | 6269430 A | 9/1994 |
| JP | 6285048 A | 10/1994 |
| JP | 7001273 B2 | 1/1995 |
| JP | 7124138 A | 5/1995 |
| JP | 7136150 A | 5/1995 |
| JP | 3116259 B | 6/1995 |
| JP | 3116260 B | 6/1995 |
| JP | 7155311 A | 6/1995 |
| JP | 7155313 A | 6/1995 |
| JP | 3238813 B2 | 7/1995 |
| JP | 7171139 A | 7/1995 |
| JP | 3134144 B | 9/1995 |
| JP | 7236625 A | 9/1995 |
| JP | 7246191 A | 9/1995 |
| JP | 8256996 A | 10/1996 |
| JP | 9192120 A | 7/1997 |
| JP | 10216113 A | 8/1998 |
| JP | 10216114 A | 8/1998 |
| JP | 10216115 A | 8/1998 |
| JP | 10337282 | 12/1998 |
| JP | 11019074 A | 1/1999 |
| JP | 11155841 A | 6/1999 |
| JP | 11-188019 | 7/1999 |
| JP | 11244268 | 9/1999 |
| JP | 20107157 A | 4/2000 |
| JP | 20237170 A | 9/2000 |
| JP | 21245871 A | 9/2001 |
| JP | 22224088 A | 8/2002 |
| JP | 22282242 A | 10/2002 |
| JP | 23153881 A | 5/2003 |
| JP | 23153882 A | 5/2003 |
| JP | 23169791 A | 6/2003 |
| JP | 23194714 A | 7/2003 |
| JP | 23210438 A | 7/2003 |
| JP | 23275192 A | 9/2003 |
| JP | 23339678 A | 12/2003 |
| JP | 24008572 A | 1/2004 |
| JP | 24089546 A | 3/2004 |
| JP | 24113353 A | 4/2004 |
| JP | 24135854 A | 5/2004 |
| JP | 24148069 A | 5/2004 |
| JP | 24148070 A | 5/2004 |
| JP | 24159810 A | 6/2004 |
| JP | 24166775 A | 6/2004 |
| JP | 24194908 A | 7/2004 |
| JP | 24202190 A | 7/2004 |
| JP | 24248819 A | 9/2004 |
| JP | 24248820 A | 9/2004 |
| JP | 24261364 A | 9/2004 |
| JP | 24290412 A | 10/2004 |
| JP | 24290544 A | 10/2004 |
| JP | 24290545 A | 10/2004 |
| JP | 24329406 A | 11/2004 |
| JP | 24329607 A | 11/2004 |
| JP | 24329928 A | 11/2004 |
| JP | 04351107 | 12/2004 |
| JP | 24337605 A | 12/2004 |
| JP | 24344367 A | 12/2004 |
| JP | 0534472 | 2/2005 |
| WO | WO 98/09566 A1 | 10/1989 |

| | | | |
|---|---|---|---|
| WO | WO 90/001293 A1 | 2/1990 |
| WO | WO 90/04352 | 5/1990 |
| WO | WO 91/01678 A1 | 2/1991 |
| WO | WO 91/11137 A1 | 8/1991 |
| WO | WO 92/00513 | 1/1992 |
| WO | WO 92/21281 A1 | 12/1992 |
| WO | WO 93/09711 | 5/1993 |
| WO | WO 93/13706 A2 | 7/1993 |
| WO | WO 93/16629 A1 | 9/1993 |
| WO | WO 94/03102 A1 | 2/1994 |
| WO | WO 94/23643 A1 | 10/1994 |
| WO | WO 95/02358 | 1/1995 |
| WO | WO 95/12349 A1 | 5/1995 |
| WO | WO 95/16970 | 6/1995 |
| WO | WO 96/13208 | 5/1996 |
| WO | 96/39927 A1 | 12/1996 |
| WO | WO 97/36536 | 10/1997 |
| WO | WO 97/36538 | 10/1997 |
| WO | WO 97/49330 A1 | 12/1997 |
| WO | WO 98/17174 A1 | 4/1998 |
| WO | WO 98/18382 | 5/1998 |
| WO | WO 98/43071 A1 | 10/1998 |
| WO | WO 98/51212 A1 | 11/1998 |
| WO | WO 98/57577 A1 | 12/1998 |
| WO | WO 99/00053 | 1/1999 |
| WO | WO 99/32030 A1 | 7/1999 |
| WO | WO 99/47039 A1 | 9/1999 |
| WO | WO 99/63884 | 12/1999 |
| WO | WO 00/21438 A1 | 4/2000 |
| WO | WO 00/28888 A1 | 5/2000 |
| WO | WO 00/59374 A1 | 10/2000 |
| WO | WO 01/13790 | 3/2001 |
| WO | WO 01/17421 A1 | 3/2001 |
| WO | WO 01/47426 | 3/2001 |
| WO | WO 0116577 | 3/2001 |
| WO | WO 01/40776 A1 | 6/2001 |
| WO | WO 01/67946 | 9/2001 |
| WO | WO 01/76461 A1 | 10/2001 |
| WO | WO 02/14793 A3 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 A1 | 1/2003 |
| WO | WO 03/001180 | 1/2003 |
| WO | WO 03/009750 A3 | 2/2003 |
| WO | WO 03/011127 A1 | 2/2003 |
| WO | WO 03/020129 | 3/2003 |
| WO | WO 03024303 | 3/2003 |
| WO | WO 03/039326 A3 | 5/2003 |
| WO | WO 03/063697 | 8/2003 |
| WO | WO 03/063697 A1 | 8/2003 |
| WO | WO 03/073924 A1 | 9/2003 |
| WO | WO 2004/000114 | 12/2003 |
| WO | WO 2004/006748 A3 | 1/2004 |
| WO | WO 2004/069046 | 8/2004 |
| WO | WO 2004/075746 A2 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 A2 | 3/2005 |
| WO | WO 2005/065540 | 7/2005 |
| WO | WO 2006/104790 | 10/2006 |

OTHER PUBLICATIONS

Rheineck-Leyssius, Aart t.; et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M. et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P. et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings* of the 20th annual International Conference of the IEEE Engineering in Medicine and Biology Society, vol. 20, No. 4, pp. 1906-1909 (Oct. 1998).

Yang, Boo-Ho, et al.; "Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethymography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Atlanta Georgia, p. 786.

Rohling, Roman et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencom*, pp. 1109-1112 (1999).

Kaestle, S.; "An Algorithm for Reliable Processing of Pulse Oximetry Signals Under strong Noise Conditions," *Dissertion Book*, Lubeck University, Germany (1999).

Seelbach-Göbel Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.;* vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English Summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal Surface motion measurement for continuous monitoring of respiratory function," *Proc. Instn Mech Engrs*, V215, Part H; pp. 515-520 (2001).

Gehring Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A. et al.; "Investigation of oesophageal photoplethysmographic signals and blood oxygen saturation measurements in cardiothoracic surgery patients," Physiological Measurement, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; "Multiple diagnosis based on Photoplethysmography: hematocrib, SpO2, pulse and respiration," *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25$^{th}$ Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmorgraphic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25$^{th}$ Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceedings of the 25$^{th}$ Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceedings of the 25$^{th}$ Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25$^{th}$ Annual International Conference of the IEEE, EMBS*, Cancun, Mexico; Sep. 17-21, 2003; pp. 1394-1397

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximeter with Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th *International conference of the IEEE EMBS,* San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing,* vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS,* San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia,* vol. 59, pp. 390-393 (2004).

Johnston, William S., et al.; "Effects of Motion Artifacts on helmet-Mounted Pulse Oximeter Sensors," 2 pgs. (2004)

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing,* vol. 18, pp. 75-79 (2004).

Heuss, Ludwig T., et al.; "Combined Pulse Oximetry / Cutaneous Carbon dioxide Tension Monitoring During Colonscopies: Pilot study with a Smart Ear Clip," *Digestion,* vol. 70, pp. 152-158 (2004).

Matsuzawa, Y., et al.; "Pulse Oximeter," *Home Care Medicine,* pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE,* vol. 5459, pp. 38-45 (2004).

Johnston, W.S., et al.; "Extracting Breathing Rate Information from a Wearable Reflectance Pulse Oximeter Sensor," *Proceedings of the 26th Annual International conference of the IEEE EMBS,* San Francisco, California; Sep. 1-5, 2004; pp. 5388-5391.

Spigulis, Janis, et al.; "Optical multi-channel sensing of skin blood pulsations," *Optical Sensing, Proceedings of SPIE,* vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation,* vol. 2, No. 3 (9 pages) (Mar. 2005).

Urquhart, C., "Ear probe pulse oximeters and neonates," *Anaesthesia,* vol. 60, p. 294 (2005).

Jonnson, P.O. "Patent Cooperation Treaty PCT Written Opinion of the International Searching Authority"; Apr. 20, 2007; 12pp.; European Patent Office; Berlin.

J. Hayoz, et al.; "World's First Combined digital Oximetry Pulse Oximetry Carbon Dioxide Tension Ear Sensor", *Abstracts,* A6, p. S103. (undated).

J. Huang, et al.; "Low Power Motion Tolerant Pulse Oximetry," *Abstracts,* A7, p. S103. (undated).

P. Lang, et al.; "Signal Identification and Quality Indicator™ for Motion Resistant Pulse Oximetry," *Abstracts,* A 10, p. S105. (undated).

R. Neumann, et al.; "Fourier Artifact suppression Technology Provides Reliable $SpO_2$," *Abstracts,* A11, p. S105. (undated).

Hamilton, Patrick S., et al.; "Effect of Adaptive Motion-Artifact Reduction on QRS Detection," *Biomedical Instrumentation & Technology,* pp. 197-202 (undated).

Kim, J.M., et al.; "Signaling Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE,* pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE,* vol. 2976, pp. 78-87 (undated).

Odagiri, Y.; "Pulse Wave Measuring Device," *Micromechatronics,* vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine,* vol. 69, No. 4; pp. 53 (date unknown) (Article in Japanese—contains English summary of article).

* cited by examiner

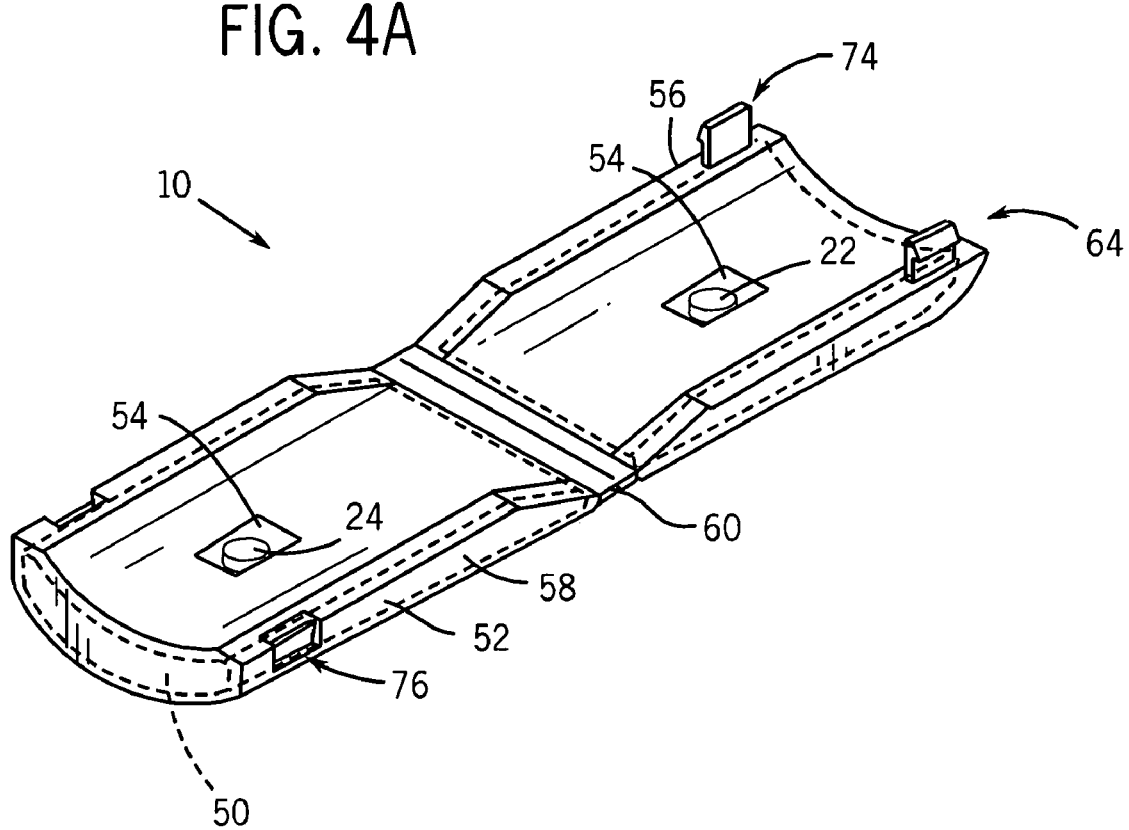
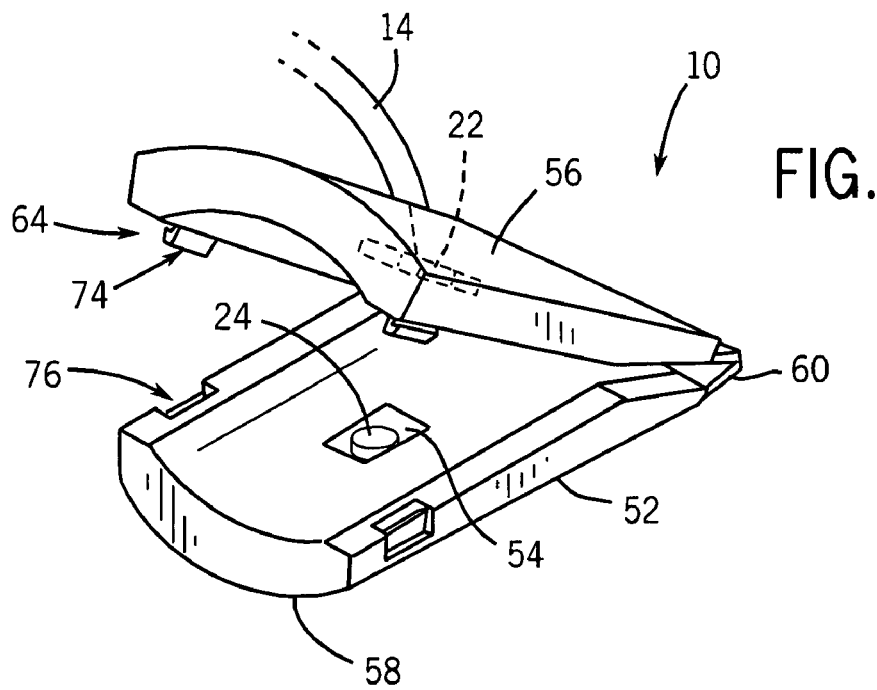

FOLDING MEDICAL SENSOR AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is reusable. One such type of pulse oximeter sensor is a clip-style sensor which is held on a patient by the force provided by a spring or other biasing mechanism. Such a clip-style sensor may then be removed by applying a countervailing force to the spring or biasing mechanism, thereby separating the ends of the sensor and allowing the sensor to be removed. In this manner, the clip-style sensor can be applied and removed many times, with the same or different patients.

Such reusable sensors, however, may be uncomfortable for the patient for various reasons. For example, the materials used in their construction may not be adequately compliant or supple or the structural features may include angles or edges. Furthermore, the reusable sensor should fit snugly enough that incidental patient motion will not dislodge or move the sensor, yet not so tight that it may interfere with pulse oximetry measurements. Such a conforming fit may be difficult to achieve over a range of patient physiologies without adjustment or excessive attention on the part of medical personnel. In addition, lack of a tight or secure fit may allow light from the environment to reach the photodetecting elements of the sensor. Such environmental light is not related to a physiological characteristic of the patient and may, therefore, introduce error into the measurements derived using data obtained with the sensor.

Reusable pulse oximeter sensors are also used repeatedly and, typically, on more than one patient. Therefore, over the life of the sensor, detritus and other bio-debris (sloughed off skin cells, dried fluids, dirt, and so forth) may accumulate on the surface of the sensor or in crevices and cavities of the sensor, after repeated uses. As a result, it may be desirable to quickly and/or routinely clean the sensor in a thorough manner. However, in sensors having a multi-part construction, as is typical in reusable pulse oximeter sensors, it may be difficult to perform such a quick and/or routine cleaning. For example, such a thorough cleaning may require disassembly of the sensor and individual cleaning of the disassembled parts or may require careful cleaning using utensils capable of reaching into cavities or crevices of the sensor. Such cleaning is labor intensive and may be impractical in a typical hospital or clinic environment.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a sensor assembly that includes: a frame, wherein the frame is configured to move between an open and a closed configuration; a covering provided over at least part of the frame; at least one optical component disposed on the frame; and a retaining component configured to hold the frame in the closed configuration when engaged.

There is provided a sensor assembly that includes: a sensor body configured to move between an open and a closed position; an emitter disposed on the sensor body; a detector disposed on the sensor body; and a retaining component configured to hold the sensor body in the closed configuration when engaged.

There is provided a sensor assembly that includes: a frame configured to move between an open and a closed position; an emitter disposed on the frame; a detector disposed on the frame; and a covering provided over at least part of the frame to form a sensor assembly.

There is provided a method of manufacturing a sensor that includes: situating an emitter and a detector on a frame; and coating the frame with a coating material to form a sensor assembly, wherein the frame is substantially open when coated.

There is provided a method for acquiring physiological data that includes: emitting two or more wavelengths of light from an emitter of a sensor assembly, wherein the sensor assembly is held in a closed configuration by one or more retaining components; detecting transmitted or reflected light using a photodetector of the sensor assembly; and determining a physiological parameter based on the detected light.

There is provided a retaining component for use on a sensor assembly that includes: an elastic band configured to hold a sensor body in a substantially closed configuration.

There is provided a method of manufacturing a sensor body that includes: coating a frame with a coating material to form a sensor body, wherein the frame is substantially open when coated.

There is provided a sensor body that includes: a frame, wherein the frame is configured to move between an open and a closed configuration; a covering provided over at least part of the frame; and a retaining component configured to hold the frame in the closed configuration when engaged.

There is provided a sensor body that includes: a sensor body configured to move between an open and a closed position; and a retaining component configured to hold the sensor body in the closed configuration when engaged.

There is provided a sensor body that includes: a frame configured to move between an open and a closed position; and a covering provided over at least part of the frame to form a sensor assembly.

There is provided a frame of a sensor that includes: a frame configured to move between an open and a closed configuration; and a retaining component configured to hold the frame in the closed configuration when engaged.

There is provided a method for manufacturing a frame of a sensor that includes: forming a frame configured to move between an open and a closed configuration, wherein the frame comprises a retaining component configured to hold the frame in the closed configuration when engaged.

BRIEF DESCRIPTION OF THE DRAWINGS

Advantages of the invention may become apparent upon reading the following detailed description and upon reference to the drawings in which:

FIG. 4A illustrates a covered sensor in an open configuration, in accordance with aspects of the present technique;

FIG. 4B illustrates the sensor of FIG. 4A in an intermediate configuration;

DETAILED DESCRIPTION OF SPECIFIC EMBODIMENTS

Figure 1:
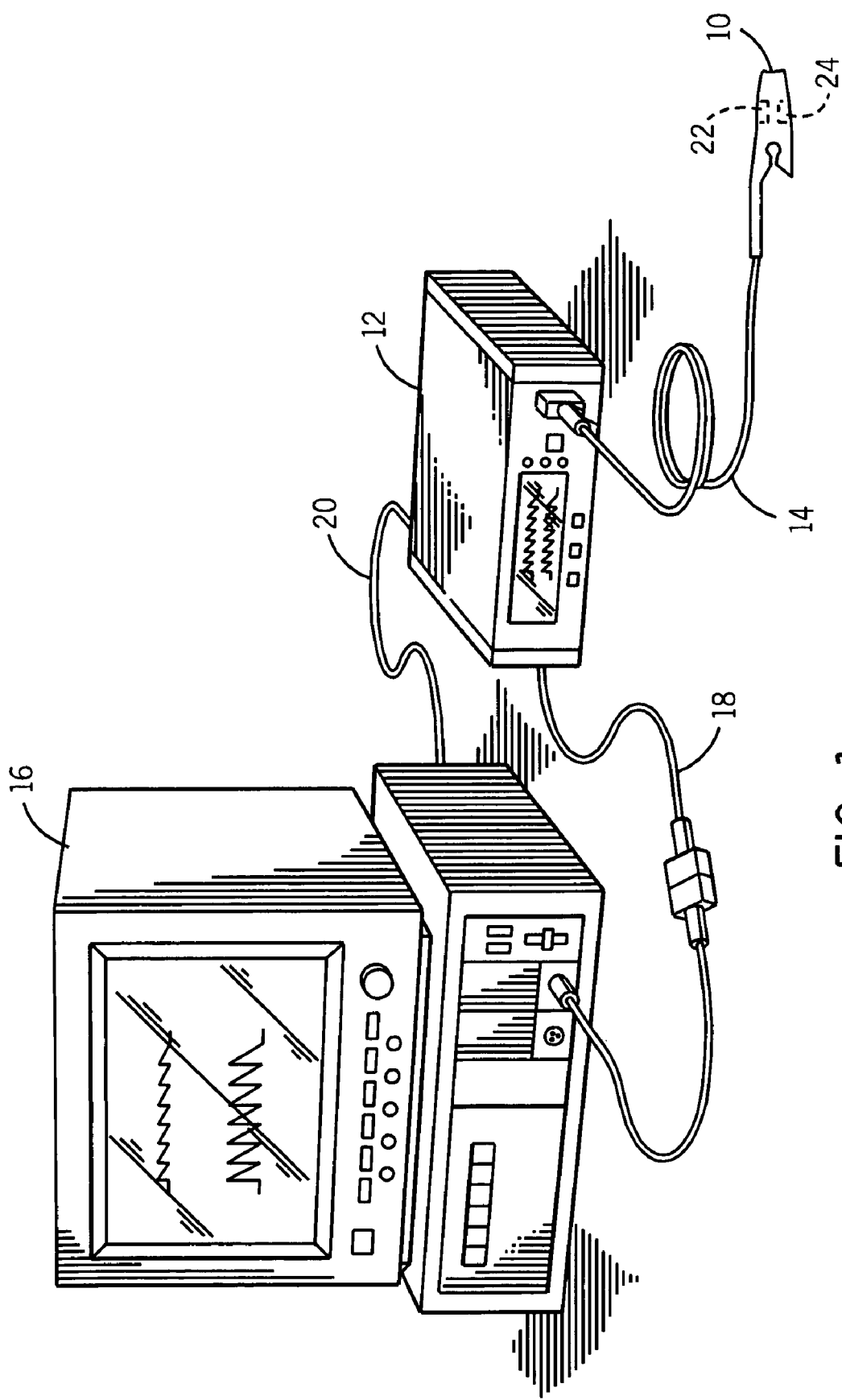
FIG. 1 illustrates a patient monitoring system coupled to a multi-parameter patient monitor and a sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a comfortable and conformable reusable patient sensor, such as for use in pulse oximetry or other applications utilizing spectrophotometry, that is easily cleaned and that is resistant to environmental light infiltration. In accordance with some aspects of the present technique, a reusable patient sensor is provided that is based upon a frame upon which the sensor components, such as light emitting diodes and photodetectors, may be situated. To simplify construction, the frame may be constructed or formed in an open configuration, as opposed to the closed configuration employed when the resulting sensor is in use. In embodiments where the sensor is constructed from an open frame, a retaining or locking mechanism may be included on the sensor to hold the sensor in a closed configuration once folded or bent into the closed configuration.

Furthermore, the sensor may be covered, such as with a coating or overmold material, to provide patient comfort and a suitably conformable fit. In such embodiments, the frame may be covered in an open configuration to reduce the labor and complexity of the overmolding process. In addition, the retaining or locking mechanism may be provided as part of the frame that is covered, as part of the frame that is not covered, as part of the overmold material alone, or as a separate structure that is added combined with the covered sensor to hold the sensor in a closed configuration when in use.

Prior to discussing such exemplary sensors in detail, it should be appreciated that such sensors may be designed for use with a typical patient monitoring system. For example, referring now to FIG. 1, a sensor 10 according to the present invention may be used in conjunction with a patient monitor 12. In the depicted embodiment, a cable 14 connects the sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor, that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors. In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or corresponding wireless transmissions) are typically used to transmit control or timing signals from the monitor 12 to the sensor 10 and/or to transmit acquired data from the sensor 10 to the monitor 12. In some embodiments, however, the cable 14 may be an optical fiber that allows optical signals to be conducted between the monitor 12 and the sensor 10.

In one embodiment, the patient monitor 12 may be a suitable pulse oximeter, such as those available from Nellcor Puritan Bennett Inc. In other embodiments, the patient monitor 12 may be a monitor suitable for measuring tissue water fractions, or other body fluid related metrics, using spectrophotometric or other techniques. Furthermore, the monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 to provide additional functions, the patient monitor 12 may be coupled to a multi-parameter patient monitor 16 via a cable 18 connected to a sensor input port and/or via a cable 20 connected to a digital communication port.

The sensor 10, in the example depicted in FIG. 1, is a reusable sensor that is covered to provide a unitary or enclosed assembly. The sensor 10 includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 that is responsible for transmitting electrical and/or optical signals to and from the emitter 22 and detector 24 of the sensor 10. The cable 14 may be permanently coupled to the sensor 10, or it may be removably coupled to the sensor 10—the latter alternative being more useful and cost efficient in situations where the sensor 10 is disposable.

The sensor 10 described above is generally configured for use as a "transmission type" sensor for use in spectrophotometric applications, though in some embodiments it may instead be configured for use as a "reflectance type sensor." Transmission type sensors include an emitter and detector that are typically placed on opposing sides of the sensor site. If the sensor site is a fingertip, for example, the sensor 10 is positioned over the patient's fingertip such that the emitter and detector lie on either side of the patient's nail bed. For example, the sensor 10 is positioned so that the emitter is located on the patient's fingernail and the detector is located opposite the emitter on the patient's finger pad. During operation, the emitter shines one or more wavelengths of light through the patient's fingertip, or other tissue, and the light received by the detector is processed to determine various physiological characteristics of the patient.

Reflectance type sensors generally operate under the same general principles as transmittance type sensors. However, reflectance type sensors include an emitter and detector that are typically placed on the same side of the sensor site. For example, a reflectance type sensor may be placed on a patient's fingertip such that the emitter and detector are positioned side-by-side. Reflectance type sensors detect light photons that are scattered back to the detector.

For pulse oximetry applications using either transmission or reflectance type sensors the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

Pulse oximetry and other spectrophotometric sensors, whether transmission-type or reflectance-type, are typically placed on a patient in a location conducive to measurement of the desired physiological parameters. For example, pulse oximetry sensors are typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, forehead, or earlobes. Regardless of the placement of the sensor 10, the reliability of the pulse oximetry measurement is related to the accurate detection of transmitted light that has passed through the perfused tissue and has not been inappropriately supplemented by outside light sources or modulated by subdermal anatomic structures. Such inappropriate supplementation and/or modulation of the light transmitted by the sensor can cause variability in the resulting pulse oximetry measurements.

As noted above, the sensor 10 discussed herein may be configured for either transmission or reflectance type sensing. For simplicity, the exemplary embodiment of the sensor 10 described herein is adapted for use as a transmission-type sensor. As will be appreciated by those of ordinary skill in the art, however, such discussion is merely exemplary and is not intended to limit the scope of the present technique.

Figure 2A:
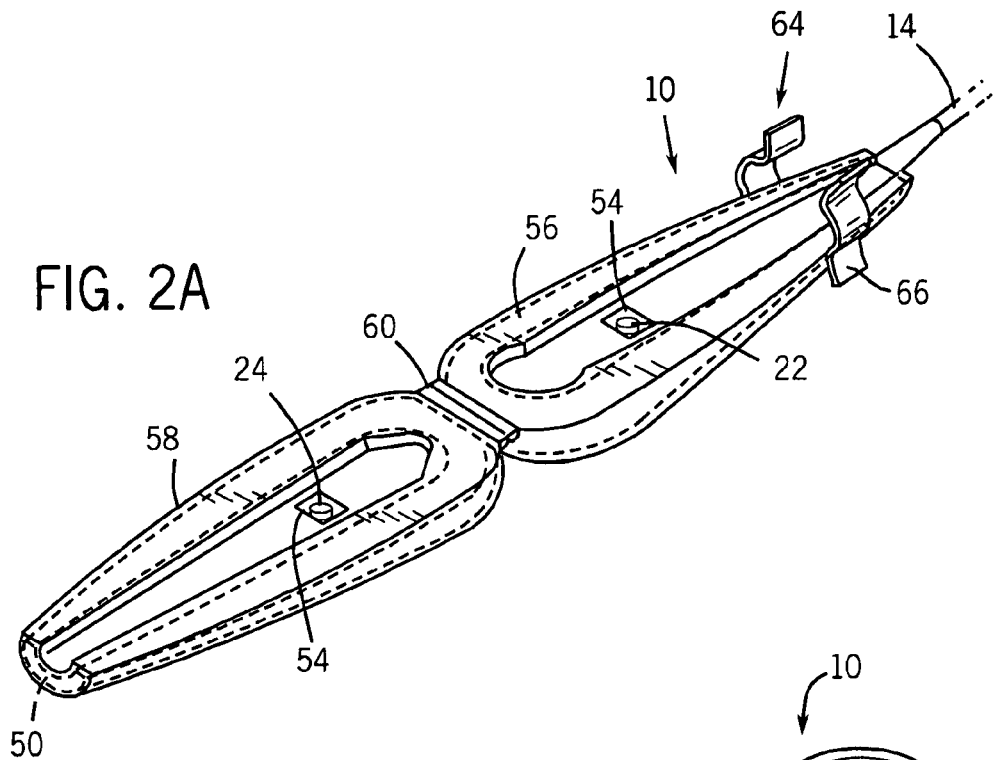
FIG. 2A illustrates a covered sensor in an open configuration, in accordance with aspects of the present technique.
Figure 2B:
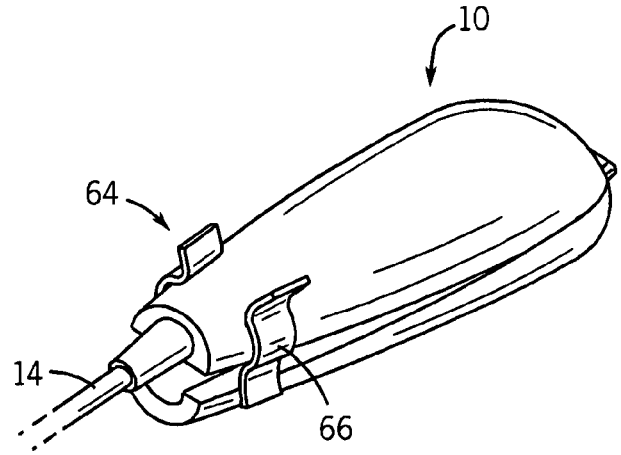
FIG. 2B illustrates the sensor of FIG. 2A in a closed configuration.

Referring now to FIGS. 2A and 2B, a first embodiment of the sensor 10 is depicted which includes a frame 50 covered with a covering material 52 in both an open and a closed configuration respectively. The frame 50 houses an emitter 22 and detector 24 within respective optical component housings. In the depicted embodiment, the emitter 22 and detector 24 are not covered by the covering material 52 and/or optically communicate through respective windows 54 that are substantially transparent to the wavelengths of interest and that are provided in the covering material 52.

In the depicted embodiment, the emitter 22 and detector 24 are provided substantially flush with the patient facing surfaces of the sensor 10, as may be suitable for pulse oximetry applications. For other physiological monitoring applications, such as applications measuring tissue water fraction or other body fluid related metrics, other configurations may be desirable. For example, in such fluid measurement applications it may be desirable to provide one or both of the emitter 22 and detector 24 recessed relative to the patient facing surfaces of the sensor 10. Such modifications may be accomplished by proper configuration or design of a mold or die used in overmolding the frame 50, as discussed below, and/or by proper design of the respective emitter housing and/or detector housing of the frame 50.

The frame 50 may be solid or skeletal (i.e., a framework of spaced apart beams and struts) depending on the rigidity and solidity desired of the frame 50. In addition the frame 50 may include different structures or regions composed of different materials or which have different physical properties, such as rigidity, elasticity, and so forth. The frame 50 generally defines the shape of the sensor 10 when coated, though, in some embodiments, portions of the sensor 10 may be formed from the covering material 52 without corresponding underlying frame structures. Alternatively, in other embodiments, portions of the frame 50 may not be covered and may form part of the exposed surface of the sensor 10. Indeed, though the sensor 10 is depicted in an exemplary covered embodiment, in other embodiments, the frame 50 may not be covered but may instead primarily constitute the sensor body.

In certain embodiments, the frame 50 may be constructed, in whole or in part, from polymeric materials, such as thermoplastics, capable of providing a suitable rigidity or semi-rigidity for the different portions of the frame 50. Examples of such suitable materials include polyurethane, polypropylene and nylon, though other polymeric materials may also be suitable. In other embodiments, the frame 50 is constructed, in whole or in part, from other suitably rigid or semi-rigid materials, such as stainless steel, aluminum, magnesium, graphite, fiberglass, or other metals, alloys, or compositions that are sufficiently ductile and/or strong. For example, metals, alloys, or compositions that are suitable for diecasting, sintering, lost wax casting, stamping and forming, and other metal or composition fabrication processes may be used to construct the frame 50.

In addition, the frame 50 may be constructed as an integral structure or as a composite structure. For example, in one embodiment, the frame 50 may be constructed as a single piece from a single material or from different materials. Alternatively, the frame 50 may be constructed or assembled from two or more parts that are separately formed. In such embodiments, the different parts may be formed from the same or different materials. For example, in implementations where different parts are formed from different materials, each part may be constructed from a material having suitable mechanical and/or chemical properties for that part. The different parts may then be joined or fitted together to form the frame 50.

In addition, the frame 50 may be molded, formed, or constructed in a different configuration than the final sensor configuration or may be adjustable to various configurations. For example, the frame 50 for use in the sensor 10 may be initially formed in a generally open configuration or may be adjustable to such an open configuration. In such an embodiment, the frame 50 may be formed or adjusted to be in an open configuration such that the included angle (i.e., the angle formed by the top portion 56 and bottom portion 58 of the frame 50 pivoting about hinge region 60) is between about 5° to about 280°. In one embodiment, as will be appreciated by those of ordinary skill in the art, the open configuration may be a substantially flat configuration, i.e., a configuration having an included angle of approximately 180°, as depicted in FIG. 2A.

In forming or adjusting the frame 50 in an open configuration, an included angle may be selected which facilitates subsequent manipulation and use of the frame 50. The included angle of the frame 50 may be chosen to facilitate or ease such tasks as inserting the emitter 22 and/or detector 24 within their respective housings, connecting signal transmission structures (such as flex circuitry) to the emitter 22 and/or detector 24, and/or covering the frame 50, and any attached components, with a covering material 52, such as an overmold material. During some or all of these different processes, the included angle of the frame 50 may be adjusted to facilitate the ongoing process. For example, the frame 50 may be provided in a flat configuration, i.e., 180° included angle, during the installation of optical components and conductive circuitry but may be adjusted to another included angle, such as 120°, for overmolding, or vice versa. The sensor 10, and therefore the frame 50, may be bent from the open configuration into a relatively closed configuration, as depicted in FIG. 2B, for subsequent use on a patient.

For example, in one embodiment, the frame 50 is overmolded in a relatively flat configuration to simplify the overmolding process, resulting in a sensor 10 as depicted in FIG. 2A. In one implementation, the covering material 52 is a thermoplastic elastomer or other conformable coating or material. In such embodiments, the thermoplastic elastomer may include compositions such as thermoplastic polyolefins, thermoplastic vulcanizate alloys, silicone, thermoplastic polyurethane, and so forth. As will be appreciated by those of ordinary skill in the art, the overmolding composition may vary, depending on the varying degrees of conformability, durability, wettability, elasticity, or other physical and/or chemical traits that are desired.

Selection of an overmold material as the covering material 52 may be based upon the desirability of a chemical bond between the frame 50 and the covering material 52. Such a chemical bond may be desirable for durability of the resulting overmolded sensor 10. For example, to prevent separation of the covering material 52 from the frame 50, a covering material 52 may be selected which bonds with some or all of the frame 50 once overmolded. In such embodiments, the covering material 52 and the portions of the frame 50 to which the covering material 52 is bonded are not separable, i.e., they form one continuous and generally inseparable structure.

Furthermore, in embodiments in which the covering material 52 employed is liquid or fluid tight, the sensor 10 may be easily maintained, cleaned, and/or disinfected by immersing the sensor into a disinfectant or cleaning solution or by rinsing the sensor 10 off, such as under running water. For example, in an open configuration of the sensor 10, as depicted in FIG. 2A, the sensor 10 may be immersed or rinsed with water or a disinfectant solution for easy cleaning. Of course, the sensor 10 may be cleaned in either the closed or open configuration. In particular, the covered sensor 10 may be generally or substantially free of crevices, gaps, junctions or other surface irregularities typically associated with a multi-part construction which may normally allow the accumulation of biological detritus or residue. Such an absence of crevices and other irregularities may further facilitate the cleaning and care of the sensor 10.

In an embodiment in which the frame 50 is completely or substantially covered, the resulting sensor 10 is formed as a unitary or integral sensor assembly. In one embodiment, the sensor 10 is formed by an injection molding process. In such an embodiment the frame 50, may be positioned within a die or mold of the desired shape for the sensor 10. A molten or otherwise unset overmold material may then be injected into the die or mold. For example, in one implementation, a molten thermoplastic elastomer at between about 400° F. to about 450° F. is injected into the mold. The overmold material may then be set, such as by cooling for one or more minutes or by chemical treatment, to form the sensor body about the frame 50. In certain embodiments, other sensor components, such as the emitter 22 and/or detector 24, may be attached or inserted into their respective housings or positions on the overmolded sensor body.

Alternatively, the optical components (such as emitter 22 and detector 24) and/or conductive structures (such as wires or flex circuits) may be placed on the frame 50 prior to overmolding. The frame 50 and associated components may then be positioned within a die or mold and overmolded, as previously described. To protect the emitter 22, detector 24, and or other electrical components, conventional techniques for protecting such components from excessive temperatures may be employed. For example, the emitter 22 and/or the detector 24 may include an associated clear window 54, such as a plastic or crystal window, in contact with the mold to prevent coating from being applied over the window. In one embodiment, the material in contact with such windows may be composed of a material, such as beryllium copper, which prevents the heat of the injection molding process from being conveyed through the window to the optical components. For example, in one embodiment, a beryllium copper material initially at about 40° F. is contacted with the windows associated with the emitter 22 and/or detector 24 to prevent coating of the windows and heat transfer to the respective optical components.

As will be appreciated by those of ordinary skill in the art, the injection molding process described herein is merely one technique by which the frame 50 may be covered to form a sensor body, with or without associated sensing components. Other techniques which may be employed include, but are not limited to, dipping the frame 50 into a molten or otherwise unset coating material to coat the frame 50 or spraying the frame 50 with a molten or otherwise unset coating material to coat the frame 50. In such implementations, the coating material may be subsequently set, such as by cooling or chemical means, to form the coating. Such alternative techniques, to the extent that they may involve high temperatures, may include thermally protecting whatever optical components are present, such as by using beryllium copper or other suitable materials to prevent heat transfer through the windows associated with the optical components, as discussed above.

The frame 50 may be covered by other techniques as well. For example, the covering material 52 may be a sheet, a sleeve, or a film material which is applied to the frame. Such a covering material 52 may be bonded, such as with an adhesive material, or mechanically fastened to the frame 50. For instance, a suitable film material may be an extruded or laminated film that is adhesively or mechanically bonded to the frame 50. Likewise, a suitable sheet material may be a single or multi-layer sheet material that is adhesively or mechanically bonded to the frame 50. Other exemplary covering material 52 include cast, foamed, or extruded materials suitable for attachment to the frame 50.

By such techniques, the frame 50, as well as the optical components and associated circuitry where desired, may be encased in a covering material 52 to form the sensor 10 or a sensor body to which one or more of the optical components may be added. Such a sensor 10 may be fitted to the finger, toe, ear, or other appendage of a patient when the sensor 10 is in a closed configuration. To facilitate the fitting process, a retaining component 64 may be provided to secure the sensor 10 in a closed configuration for clinical use. For example, in the embodiment of FIGS. 2A and 2B a retaining component 64 in the form of locking tabs 66 is provided. The locking tabs 66 may be formed as a part of the frame 50 which may or may not be covered. Alternatively, the locking tabs 66 may be formed from the covering material 52 or may be a separate component that is configured to be attached to the sensor 10 prior to use on a patient.

Figure 3:
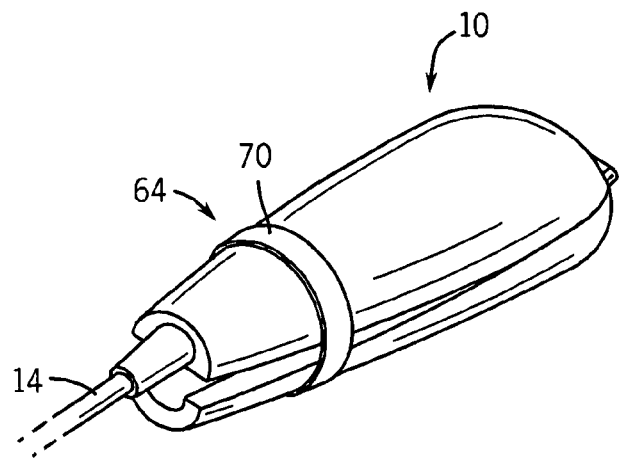
FIG. 3 illustrates a covered sensor in a closed configuration, in accordance with aspects of the present technique.

As will be appreciated by those of ordinary skill in the art, the retaining component 64, such as locking tabs 66, may be composed of a material or a combination of materials that provide the desired elasticity and resistance, such as polymeric materials (rubber, plastic, and so forth) or metals. Likewise, the retaining component 64 may take other forms than the exemplary locking tabs 66. For example, referring now to FIG. 3, a sensor 10 is depicted in which the retaining component 64 is an elastic band 70 configured to hold the sensor 10 in a closed configuration. The elastic band 70 may be formed separate from the remainder of the sensor 10 and applied prior to use. Alternatively, the elastic band 70 may be formed integrally with the sensor 10, such as in the form of an elastic strap that may be adjustably secured to maintain the sensor 10 in the desired configuration. Likewise the elastic band 70 may interface with the surface of the sensor 10 with our without an adhesive layer and/or a mechanical retention mechanism to facilitate the retention of the elastic band 70 to the sensor 10.

As will be appreciated by those of ordinary skill in the art, the retaining force provided by the retaining component 64 may be overcome or removed by a clinician in order to remove the sensor 10 from a patient or to adjust the fit of the sensor. In addition, within certain embodiments, the retaining component 64 may provide varying degrees of retention and/or separation of the top and bottom portions 56, 58 of the sensor 10. For example, in embodiments where the retaining component 64 is an elastic band 70, the elasticity of the band 70 may allow a range of retention such that different sized fingers or other digits may be accommodated by the sensor 10. Likewise, in embodiments where the retaining component 64 is provided as locking tabs 66, the locking tabs 66 may be provided with more than one locked or engaged position to provide a range of retained positions for the sensor 10. In this manner, the sensor 10 may be comfortably and conformably fitted to a patient's finger, toe, ear, and so forth.

Other retaining components or arrangements that provide similar benefits are also possible. For example, referring now to FIGS. 4A and 4B, a covered sensor 10 is depicted having a retaining component 64 in the form of a snap fit 74. The snap fit 74 may be formed from a portion of the frame 50 that is not covered or may be formed from a portion of the covering material 52, such as a portion of an overmold material having a greater durometer than the portion configured to come in contact with a patient. As depicted in FIG. 4A, the sensor 10 may be formed or provided in an open configuration, as discussed above. As depicted in FIG. 4B, the top portion 56 and bottom portion 58 may be pivoted about hinge region 60 toward a closed configuration. Once in the closed configuration the depicted snap fit 74 engages a fitted region 76 configured to conform to and complement the snap fit 74 to form a secure fit. The fitted region 76 may be formed from a portion of the covering material 52 shaped to engage the snap fit 74 and/or may be formed from a portion of the covering material having a durometer sufficient to form a good fit with the snap fit 74 but sufficiently compliant to be engaged by the snap fit 74.

Figure 5A:
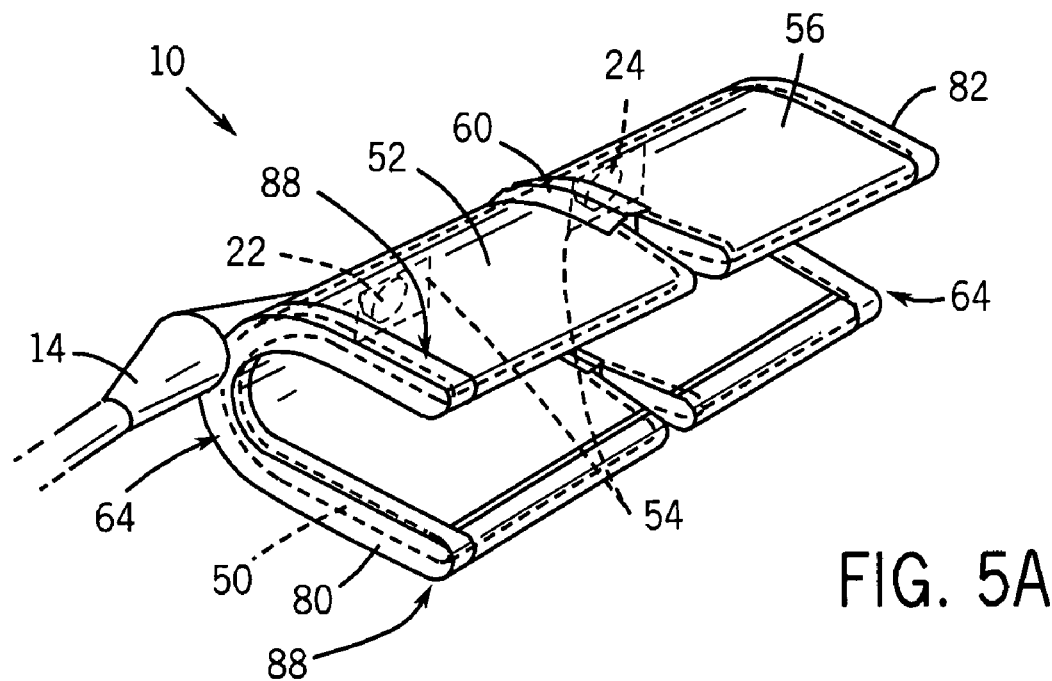
FIG. 5A illustrates a covered sensor in an open configuration, in accordance with aspects of the present technique.
Figure 5B:
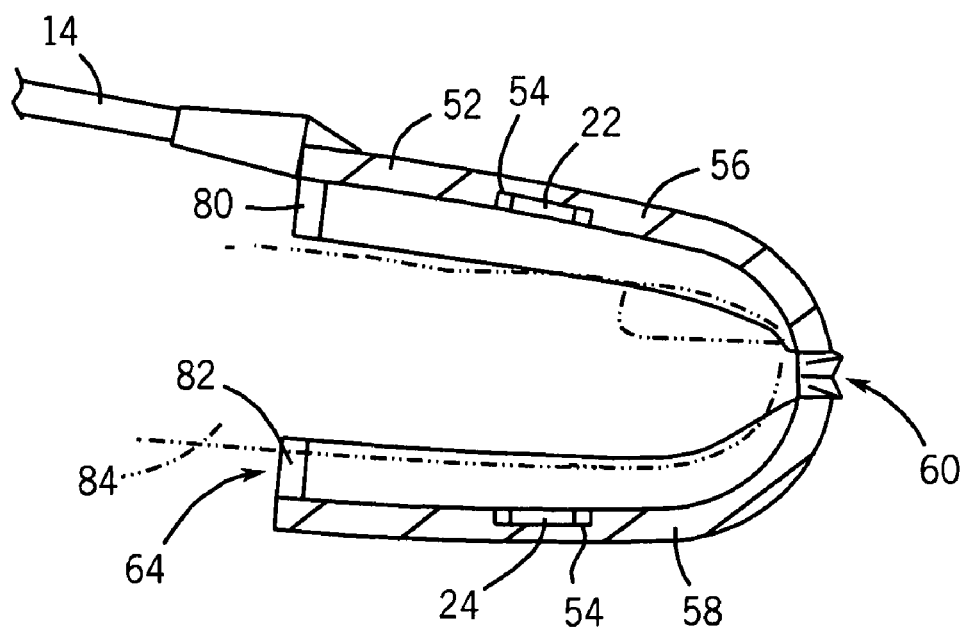
FIG. 5B illustrates the sensor of FIG. 5A in a closed configuration.

Similarly, referring now to FIGS. 5A and 5B, the retaining component 64 may be formed by a first and a second portion 80, 82 of the sensor 10 which are configured to form an interference fit when engaged. In this embodiment, the sensor 10 may be formed or adjusted to an open configuration, as depicted in FIG. 5A. Upon closing the sensor 10, such as about a finger 84, the first portion 80, here depicted as the male portion of the interference fit, is interferingly engaged with the second portion, i.e., the female portion of the interference fit. The first portion 80 and/or the second portion 82 may be formed from respective portions of the frame 50 that are not covered or may be formed from respective portions of the covering material 52 having suitable durometers for the formation of the interference fit.

In addition, as illustrated in FIG. 5A, flaps or side extensions 88 of the covering material 52 on the sides of the sensor 10 are depicted which facilitate the exclusion of environmental or ambient light from the interior of the sensor 10. Such extensions help prevent or reduce the detection of light from the outside environment, which may be inappropriately detected by the sensor 10 as correlating to the $SaO_2$. Thus, the pulse oximetry sensor may detect differences in signal modulations unrelated to the underlying $SaO_2$ level. In turn, this may impact the detected red-to-infrared modulation ratio and, consequently, the measured blood oxygen saturation ($SpO_2$) value. The conformability of the fit of sensor 10 and the use of side extensions 88, therefore, may help prevent or reduce such errors.

While the exemplary sensors 10 discussed herein are provided as examples, other such devices are also contemplated and fall within the scope of the present disclosure. For example, other medical sensors and/or contacts applied externally to a patient may be advantageously applied using a sensor body as discussed herein. Examples of such sensors or contacts may include glucose monitors or other sensors or contacts that are generally held adjacent to the skin of a patient such that a conformable and comfortable fit is desired. Similarly, and as noted above, devices for measuring tissue water fraction or other body fluid related metrics may utilize a sensor as described herein. Likewise, other spectrophotometric applications where a probe is attached to a patient may utilize a sensor as described herein.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well. Likewise, the present techniques are not limited to use on fingers and toes but may also be applied to placement on other body parts such as in embodiments configured for use on the ears or nose.

What is claimed is:

1. A sensor assembly, comprising:
   a frame configured to move between an open and a closed configuration;
   a covering provided over at least part of the frame, wherein the covering comprises a thermoplastic elastomer;
   at least one optical component disposed on the frame; and
   a retaining component configured to hold the frame in the closed configuration when the retaining component is engaged.

2. The sensor assembly of claim 1, wherein the covering comprises a sheet, a sleeve or a film material.

3. The sensor assembly of claim 1, wherein the covering is bonded to the frame.

4. The sensor assembly of claim 1, wherein the covering is mechanically fastened to the frame.

5. The sensor assembly of claim 1, wherein the thermoplastic elastomer comprises at least one of a thermoplastic polyolefin, a thermoplastic vulcanizate alloy, thermoplastic polyurethane, silicone, or a combination thereof.

6. The sensor assembly of claim 1, wherein the thermoplastic elastomer comprises an extruded or laminated film.

7. The sensor assembly of claim 1, wherein the retaining component is integral with the sensor assembly.

8. The sensor assembly of claim 1, wherein the retaining component is separable from the sensor assembly.

9. The sensor assembly of claim 1, wherein the retaining component comprises a mechanical fastener, a band, a snap fit, an interference fit, a portion of the frame, a portion of the covering, or a combination thereof.

10. The sensor assembly of claim 1, wherein the open configuration comprises an included angle in the range of about 120 to about 280 degrees.

11. The sensor assembly of claim 1, wherein the open configuration comprises an included angle of approximately 180 degrees.

12. The sensor assembly of claim 1, wherein the sensor assembly comprises at least one of a pulse oximetry sensor, a sensor for measuring a water fraction, or a combination thereof.

13. The sensor assembly of claim 1, wherein the sensor assembly is fluid tight.

14. The sensor assembly of claim 1, wherein the frame comprises a single molded part.

15. The sensor assembly of claim 1, wherein the frame comprises two or more parts joined to form the frame.

16. A sensor assembly, comprising:
    a sensor body configured to move between an open and a closed position;
    a covering provided over at least part of the sensor body, wherein the covering comprises a thermoplastic elastomer;
    an emitter disposed on the sensor body;
    a detector disposed on the sensor body; and
    a retaining component configured to hold the sensor body in the closed configuration when the retaining component is engaged.

17. A sensor body, comprising:
    a frame configured to move between an open and a closed configuration;
    a covering provided over at least part of the frame, wherein the covering comprises a thermoplastic elastomer; and
    a retaining component configured to hold the frame in the closed configuration when the retaining component is engaged.

18. A sensor, comprising:
    a skeletal frame having a thermoplastic elastomer overmolding, wherein the skeletal frame is configured to move between an open and a closed configuration; and
    a retaining component configured to hold the skeletal frame in the closed configuration when the retaining component is engaged.

19. A method for manufacturing a frame of a sensor, comprising:
    forming a frame configured to move between an open and a closed configuration, wherein the frame comprises a retaining component configured to hold the frame in the closed configuration when the retaining component is engaged; and
    overmolding at least part of the frame with a thermoplastic elastomer.

20. The method of claim 19, wherein forming the frame comprises performing at least one of a molding operation, a diecasting operation, a sintering operation, a casting operation, or a stamping operation.

* * * * *